«12» United States Patent
Ku et al.

(10) Patent No.: US 8,257,759 B2
(45) Date of Patent: Sep. 4, 2012

(54) ANTITUSSIVE COMPOSITION AND METHOD FOR MAKING THE SAME

(75) Inventors: Yuan-Ling Ku, Taipei County (TW);
Chien-Jen Shih, Taipei County (TW);
Hsiao-Chu Huang, Taipei County (TW);
Chun-Hung Kuo, Taipei County (TW);
Yi-Chen Lin, Taipei County (TW);
Yueh-Chu Chen, Taipei County (TW);
Feng-Nien Ko, Taipei County (TW)

(73) Assignee: Medical and Pharmaceutical Industry Technology and Development Center, New Taipei (TW)

( * ) Notice: Subject to any disclaimer, the term of this patent is extended or adjusted under 35 U.S.C. 154(b) by 645 days.

(21) Appl. No.: 12/344,219

(22) Filed: Dec. 25, 2008

(65) Prior Publication Data

US 2010/0166890 A1    Jul. 1, 2010

(51) Int. Cl.
*A61K 36/00* (2006.01)

(52) U.S. Cl. .................. 424/773; 424/775; 424/725

(58) Field of Classification Search .................. None
See application file for complete search history.

(56) References Cited

U.S. PATENT DOCUMENTS 6,855,343 B2 *   2/2005   Hsu et al. .................. 424/725

OTHER PUBLICATIONS

Shi et al. "Phenolic Constituents of the Root Bark of Chinese Morus australis", Natural Medicines vol. 55,(3), pp. 143-146 (2001).*
Nomura et al "Components of Root Bark Morus australis", Journal of Medicinal Plant Research, 1983, vol. 49, pp. 90-94.*
Skoog et al., "Fundamentals of Analytical Chemistry", 7th ed., p. 702.

* cited by examiner

*Primary Examiner* — Christopher R. Tate
*Assistant Examiner* — Deborah A. Davis
(74) *Attorney, Agent, or Firm* — Pai Patent & Trademark Law Firm; Chao-Chang David Pai

(57) ABSTRACT

An antitussive composition is provided. A pharmaceutical composition for relieving, preventing and/or treating a cough includes a sufficient amount of the *Morus australis* Poir extract as an active component. The effective *Morus australis* Poir extract is prepared by extracting the root-bark of the *Morus australis* Poir with water, ethanol, acetone, ethyl acetate, or a combination thereof. The crude extract can be further fractioned by ultrafiltration or reverse phase column.

14 Claims, No Drawings

ANTITUSSIVE COMPOSITION AND METHOD FOR MAKING THE SAME

BACKGROUND OF THE INVENTION

1. Field of the Invention

The present invention relates to a pharmaceutical composition, and in particular to an antitussive composition containing *Morus australis* Poir extract as an active antitussive component and the method for making the same.

2. Description of the Related Art

*Morus alba* L. belongs to the *Moraceae* genus. White Mulberry Root-bark is the dry root bark of the *Morus alba* L, which is known as SANGBAIPI (rendered herein in accordance with the Chinese Romanization pinyin standard) in traditional Chinese medicine.

In the Chinese Medicine Pharmacopoeia, a White Mulberry Root-bark is described as being generally quilled, channeled or flat pieced, twisted, varying in length and width, 1.5 to 4 mm thick. Outer surface white or pale yellowish-white, relatively even, some with orange-yellow or brownish-yellow remains of scaly bark; inner surface yellowish-white or grayish-yellow, with fine longitudinal striations. Texture light and tenacious, strongly fibrous, uneasily broken, but easily stripped longitudinally, dusting on stripping. Odour, slight; taste, slightly sweet.

In the Traditional Chinese Medicine, the fruit of the White Mulberry is used to treat premature graying of hair, to "tonify" the blood, and treat constipation and diabetes. The bark of the White Mulberry is used to treat wheezing, edema, and to promote urination.

White Mulberry Root-bark is a traditional Chinese medicine for anti-inflammatory, diuretic, and anti-tussive application. However, the natural amount of *Morus alba* L. is not popular in Taiwan. In order to manufacture an antitussive agent having commercial value, inventor attempts to use *Morus australis* Poir. which is popular in Taiwan to prepare a new antitussive composition.

BRIEF SUMMARY OF THE INVENTION

The invention provides an antitussive composition, comprising: a sufficient amount of the *Morus australis* Poir. extract, and a pharmaceutically acceptable carrier or excipient, wherein the *Morus australis* Poir extract is extracted with water, ethanol, acetone, ethyl acetate, or a combination thereof.

The invention also provides an antitussive composition for treating a cough, comprising: a sufficient amount of the *Morus australis* Poir extract; and a pharmaceutically acceptable carrier or excipient, wherein the *Morus australis* Poir extract is prepared by the steps of: extracting the roots (or root-bark) of the *Morus australis* Poir with water, ethanol, acetone, ethyl acetate, or a combination thereof to obtain a crude extract; filtering the crude extract by a filter to obtain a filtrate; concentrating the filtrate by 10 times and then adding an equal amount of water to obtain a concentrate; loading the concentrate to a reverse phase column; eluting the reverse phase column with an ethanol solution, and collecting the ethanol eluate.

The invention also provides a method for preparing an antitussive composition, comprising extracting the roots (or root-bark) of the *Morus australis* Poir with water, ethanol, acetone, ethyl acetate, or a combination thereof to obtain a crude extract.

The invention further provides a method for relieving, preventing and/or treating a cough which comprises administration of the antitussive composition, and a pharmaceutically acceptable carrier or excipient.

A detailed description is given in the following embodiments with reference to the accompanying drawings.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides an antitussive composition for relieving, preventing and/or treating a cough, including a sufficient amount of a *Morus australis* Poir extract as an active component. The effective *Morus australis* Poir extract is prepared by extracting *Morus australis* Poir with water, ethanol, acetone, ethyl acetate, or a combination thereof. After administration of 2 g/kg per body weight, coughing is reduced by more than 30%, preferably, 40%-75%.

The invention further provides a method for preparing an antitussive composition, comprising extracting the roots (or root-bark) of the *Morus australis* Poir with water, ethanol, acetone, ethyl acetate, or a combination thereof to obtain a crude extract.

Sliced pieces of the *Morus australis* Poir root (or root-bark) is self-made. As for the manufacturing steps, they include vertically cutting open the roots of the *Morus australis* Poir, peeling the root barks, and then drying sliced roots.

In on embodiment, the crude extract of the *Morus australis* Poir can be filtered by a filter and a 2 to 10 μm, preferably, 5 μm pore sized membrane sequentially to obtain a filtrate.

In another embodiment, the filtrate can be loaded onto a reverse phase column, and the reverse phase column is eluted with water and a 35-95% ethanol solution sequentially to collect the ethanol eluate.

In another embodiment, the crude extract can be filtered to obtain a filtrate. The filtrate can be concentrated by 10 times and then adding an equal amount of water to obtain a concentrate. The concentrate can be loaded onto a reverse phase column, and the reverse phase column is eluted with an ethanol solution to collect the ethanol eluate.

In one embodiment, the crude extract can be loaded onto a reverse phase column, and the reverse phase column is eluted with a water and ethanol solution sequentially to collect the ethanol eluate.

The pore size of filter is not limited. Generally, the pore size can be about 100 to 500 mesh, preferably, about 350 mesh.

The column of the reverse column can be packed with a polystyrene resin or ion exchange resin, including Diaion HP20 resin, Amberlite XAD-7HP resin, or MCI GEL CHP20P resin. The column can be packed by a ratio of 1 g dry basis of the crude extract (or concentrate)/5 g to 100 g resin.

The invention further provides a pharmaceutical composition for relieving, preventing and/or treating a cough, comprising a sufficient amount of the antitussive composition of the invention, and a pharmaceutically acceptable carrier or excipient.

EXAMPLE

Example 1

Evaluation Model

The antitussive activity of various extracts of *Morus australis* Poir is herein evaluated according to the method described by Winter C. A. et al. (J. Pharmacol. Exp. Ther. 112:99, 1954) with modification.

Duncan Hartley derived male and female guinea pigs, weighing 450±50 g, were used. Each guinea pig was placed in a 4-liter sealed chamber equipped with an ultrasonic nebulizer to provide cough-inducing irritant by aerosol. A microphone was set to amplify coughing sounds from the guinea pigs. The animals were exposed to an aerosolized solution of 10% citric acid for 10 seconds and selected if 9-15 coughs ensued in the following 5 minutes. On the next day, solvent, i.e. distilled water, or extracts were administered orally to the animals twice a day (10:00 am and 4:00 pm). The animals were again exposed to aerosolized 10% citric acid 60 minutes after the second dose administration. The inhibition activity of extracts on citric acid-induced cough was evaluated as follows: Inhibition (%)=[(Number of coughs before administration)−(Number of coughs after administration)]/(number of coughs before administration)×100%.

Sample Preparation and Antitussive Assessment Thereof

Example 2

Water Extraction and Column Separation

One kilogram of dry root-barks of the *Morus australis* Poir were heated to a boil and refluxed twice with 10 L of the water for 1 hour to obtain crude extracts, respectively. The crude extracts were then filtered with a 350 mesh sieve and the filtrates were collected, respectively. The residues were respectively mixed with 10 times the amount of water by weight for a second extraction process (1 hour), and then filtrated with a 350 mesh sieve to obtain another filtrate. The two filtrates were combined and then filtered by a 5 µm pore sized membrane to obtain water extracts, respectively.

2.1 Column Separation (1)

The above water extracts were separated by a Diaion HP20 column (Diaion, Mitsubishi Chemistry Inc.), respectively, wherein the ratio of the dry basis of the extract and resin was 1/30. After loading the extracts onto the columns, the Diaion HP20 columns were sequentially eluted by 4 times the amount of RO water and 3 times the amount of a 35-95% ethanol solution by volume to obtain ethanol eluates (samples 1-1 to 1-6), respectively. The ethanol eluates were concentrated and freeze-dried to remove the ethanol in the eluates and obtain dry powders. The yield of the above eluates is shown in Table 1. The antitussive assessment of the above eluates is shown in Table 2.

TABLE 1

| Sample No. | Ratio of dry basis and resin | Ethanol conc. (%) | Yield (%) |
|---|---|---|---|
| 1-1 | 1:31 | 35 | 4.0 |
| 1-2 | 1:29 | 50 | 3.5 |
| 1-3 | 1:29 | 60 | — |
| 1-4 | 1:29 | 95 | 4.2 |
| 1-5 | 1:35 | 50 | 4.2 |
| 1-6 | 1:41 | 50 | 6.4 |

Yield: (eluate weight/root-bark weight) × 100%

TABLE 2

| Sample No. | Amount of administration (dosage per body weight) | Inhibition rate (%) |
|---|---|---|
| 1-1 | 2 g/kg | 46 |
| 1-2 | 2 g/kg | 61 |

TABLE 2-continued

| Sample No. | Amount of administration (dosage per body weight) | Inhibition rate (%) |
|---|---|---|
| 1-3 | 2 g/kg | 50 |
| 1-4 | 2 g/kg | 40 |
| 1-5 | 2 g/kg | 43 |
| 1-6 | 2 g/kg | 69 |

2.2 Column Separation (2)

The above water extracts were separated by a Diaion HP20 column (Diaion, Mitsubishi Chemistry Inc.), respectively, wherein the ratio of the dry basis of the extract and resin was 1/20 to 1/30. After loading the extracts onto the columns, the Diaion HP20 columns were sequentially eluted by 2 to 4 times the amount of RO water and 2 to 3 times the amount of 50% ethanol solution by volume, respectively, to obtain ethanol eluates (samples 1-7 to 1-14). The ethanol eluates were then concentrated and freeze-dried to remove the ethanol in the eluates and obtain dry powders. The yield of the above eluates is shown in Table 3. The antitussive assessment of the above eluates is shown in Table 4.

TABLE 3

| Sample No. | Pore size of membrane | Ratio of dry basis and resin | Volume of eluting water | Volume of eluting ethanol | Yield (%) |
|---|---|---|---|---|---|
| 1-7 | 5 µm | 1:30 | 4 times | 3 times | 3.7 |
| 1-8 | 5 µm | 1:25 | 2.5 times | 2 times | 3.8 |
| 1-9 | 5 µm | 1:20 | 4 times | 3 times | 3.8 |
| 1-10 | 5 µm | 1:20 | 4 times | 3 times | 4.2 |
| 1-11 | 5 µm | 1:23 | 2 times | 3 times | 5.0 |
| 1-12 | — | 1:24 | 2 times | 3 times | 2.3 |
| 1-13 | — | 1:19 | 2 times | 3 times | 1.4 |
| 1-14 | — | 1:20 | 2 times | 3 times | 1.5 |

Yield: (eluate weight/root-bark weight) × 100%

TABLE 4

| Sample No. | Amount of administration (dosage per body weight) | Inhibition rate (%) |
|---|---|---|
| 1-7 | 2 g/kg | 48 |
| 1-8 | 2 g/kg | 46 |
| 1-9 | 2 g/kg | 69 |
| 1-10 | 2 g/kg | 57 |
| 1-11 | 2 g/kg | 74 |
| 1-12 | 2 g/kg | 39 |
| 1-13 | 2 g/kg | 48 |
| 1-14 | | |

Note:
Samples 1-13 and 1-14 were combined 1:1 by weight.

Example 3

95% Ethanol Extraction

One kilogram of a dry root-bark of the *Morus australis* Poir was heated to a boil and refluxed twice with 10 L of a 95% ethanol solution for 1 hour to obtain a crude extract. The crude extract was then filtered with a 350 mesh sieve and the filtrate was collected. The residue was mixed with 10 times the amount of water by weight for a second extraction process (1 hour), and then filtrated with a 350 mesh sieve to obtain another filtrate. The two filtrates were combined to obtain an ethanol extract (sample 2-1). The ethanol extract was concentrated and freeze-dried to obtain a dry powder. The yield and antitussive assessment of the extract are shown in Table 5.

TABLE 5

| Sample No. | Yield (%) | Amount of administration (dosage per body weight) | Inhibition rate (%) |
|---|---|---|---|
| 1-1 | 9.2 | 2 g/kg | 33 |

Yield: (eluate weight/root-bark weight) × 100%

Example 4

95% Ethanol Extraction and Column Separation

The dry root-bark of the *Morus australis* Poir was used. One kilogram of the dry root-bark of the *Morus australis* Poir was heated to a boil and refluxed twice with 10 L of a 95% ethanol solution for 1 hour to obtain crude extracts. The crude extracts were then filtered with a 350 mesh sieve and the filtrates were collected, respectively. The residues were mixed with 10 times the amount of water by weight for a second extraction process (1 hour), and then filtrated with a 350 mesh sieve to obtain other filtrates. The two filtrates were combined to obtain ethanol extracts, respectively.

The ethanol extracts were concentrated by 10 times under reduced pressure and then an equal amount of water by weight was added to obtain concentrates, respectively.

The above concentrates were separated by Diaion HP20 columns (Diaion, Mitsubishi Chemistry Inc.), respectively, wherein the ratio of the dry basis of the concentrate and resin was 1/20. After loading the concentrates onto the columns, the Diaion HP20 columns were eluted by 2 times the amount of a 50% ethanol solution by volume, respectively, to obtain ethanol eluates (samples 3-1 to 3-3). The ethanol eluates were then concentrated and freeze-dried to remove the ethanol in the eluates and obtain dry powders. The yield and antitussive assessment of the above eluates are shown in Table 6.

TABLE 6

| Sample No. | Ratio of dry basis and resin | Yield (%) | Amount of administration (dosage per body weight) | Inhibition rate (%) |
|---|---|---|---|---|
| 3-1 | 1:20 | 6.3 | 0.5 g/kg | 55 |
|  |  |  | 1 g/kg | 61 |
|  |  |  | 2 g/kg | 63 |
| 3-2 | 1:20 | 7.3 | 2 g/kg | 48 |
| 3-3 | 1:20 | 5.6 | 2 g/kg | 48 |

Yield: (eluate weight/root-bark weight) × 100%

Example 5

Ethyl Acetate Extraction

The dry root-bark of the *Morus australis* Poir was used. One kilogram of the root-bark of the *Morus australis* Poir was heated to a boil and refluxed twice with 10 L of an ethyl acetate solution for 1 hour to obtain a crude extract. The crude extract was then filtered with a 350 mesh sieve and the filtrate was collected. The residue was mixed with 10 times the amount of water by weight for a second extraction process (1 hour), and then filtrated with a 350 mesh sieve to obtain another filtrate. The two filtrates were combined and then filtered by a 5 μm pore sized membrane to obtain an ethyl acetate extract (sample 4-1). The extract was concentrated under reduced pressure and dried to obtain a dry powder. The yield and antitussive assessment of the extract is shown in Table 7.

TABLE 7

| Sample No. | Yield (%) | Amount of administration (dosage per body weight) | Inhibition rate (%) |
|---|---|---|---|
| 4-1 | 2.1 | 2 g/kg | 48 |

Yield: (eluate weight/root-bark weight) × 100%

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An antitussive composition comprising: an effective amount of a root-bark extract of *Morus australis* Poir, and a pharmaceutically acceptable carrier or excipient, wherein the root-bark extract of *Morus australis* Poir is prepared by extracting root barks of *Morus australis* Poir with water to obtain a crude extract; loading the crude extract onto a reverse phase column; and eluting the reverse phase column with water and a 35-95% ethanol solution sequentially to obtain said root-bark extract.

2. The antitussive composition as claimed in claim 1, wherein the crude extract is further filtered through a filter and a 5 μm pore sized membrane sequentially to obtain a filtrate.

3. The antitussive composition as claimed in claim 1, wherein the reverse phase column is packed with a polystyrene resin or ion exchange resin.

4. The antitussive composition as claimed in claim 3, wherein the column is packed by a ratio of 1 g dry basis of the crude extract/5 g to 100 g resin.

5. An antitussive composition for treating a cough, comprising an effective amount of a root-bark extract of *Morus australis* Poir; and a pharmaceutically acceptable carrier or excipient, wherein the root-bark extract of *Morus australis* Poir is prepared by extracting root-barks of *Morus australis* Poir with water to obtain a crude extract; filtering the crude extract through a filter to obtain a filtrate; concentrating the filtrate by 10 times and then adding an equal amount of water to obtain a concentrate; loading the concentrate to a reverse phase column; eluting the reverse phase column with an ethanol solution; and collecting and drying the ethanol eluate.

6. The antitussive composition as claimed in claim 5, wherein the reverse phase column is packed with a polystyrene resin or ion exchange resin.

7. The antitussive composition as claimed in claim 6, wherein the column is packed by a ratio of 1 g dry basis of the concentrate/5 g to 100 g resin.

8. A method for preparing an antitussive composition, comprising extracting root-barks of *Morus australis* Poir with water to obtain a crude extract; loading the crude extract onto a reverse phase column; and eluting the reverse phase column with water and a 35-95% ethanol solution sequentially.

9. The method as claimed in claim 8, further comprising a step of filtering the crude extract through a filter and a 5 μm pore sized membrane to obtain a filtrate.

10. A method of preparing an antitussive composition comprising extracting root-barks of *Morus australis* Poir with water to obtain a crude extract; filtering the crude extract through a filter to obtain a filtrate; concentrating the filtrate by 10 times and then adding an equal amount of water to obtain a concentrate; loading the concentrate onto a reverse phase column; eluting the reverse phase column with an ethanol solution; and collecting and drying the ethanol eluate.

11. The method as claimed in claim 10, wherein the reverse phase column is packed with a polystyrene resin or ion exchange resin.

12. The method as claimed in claim 11, wherein the column is packed by a ratio of 1 g dry basis of the concentrate/5 g to 100 g resin.

13. A method for relieving and/or treating a cough which comprises administrating the antitussive composition of claim 1 to a subject in need thereof.

14. A method for relieving and/or treating a cough which comprises administrating the antitussive composition of claim 5 to a subject in need thereof.

* * * * *